United States Patent
Hleong

(10) Patent No.: US 7,553,511 B2
(45) Date of Patent: *Jun. 30, 2009

(54) HYDROPHILIC COATINGS FOR MEDICAL IMPLEMENTS

(75) Inventor: Koon-Wah Hleong, Sunnyvale, CA (US)

(73) Assignee: Lifescan, Inc., Milpitas, CA (US)

( * ) Notice: Subject to any disclaimer, the term of this patent is extended or adjusted under 35 U.S.C. 154(b) by 390 days.

This patent is subject to a terminal disclaimer.

(21) Appl. No.: 11/285,806

(22) Filed: Nov. 22, 2005

(65) Prior Publication Data

US 2006/0078587 A1  Apr. 13, 2006

Related U.S. Application Data

(62) Division of application No. 10/137,017, filed on May 1, 2002, now Pat. No. 7,015,262.

(51) Int. Cl.
*A61M 25/06* (2006.01)
*B05D 3/00* (2006.01)

(52) U.S. Cl. ............... 427/2.28; 523/105; 604/4.01; 604/317

(58) Field of Classification Search ........... 523/105, 523/112; 604/317; 427/2.28
See application file for complete search history.

(56) References Cited

U.S. PATENT DOCUMENTS

| | | | |
|---|---|---|---|
| 3,734,874 A | 5/1973 | Kibler et al. | |
| 4,476,189 A | 10/1984 | Posey et al. | |
| 4,755,379 A | 7/1988 | Jozefonvicz et al. | |
| 4,804,719 A | 2/1989 | Weaver et al. | |
| 4,987,182 A | 1/1991 | Creasey | |
| 5,266,322 A | 11/1993 | Myers et al. | |
| 5,427,835 A | 6/1995 | Morrison et al. | |
| 5,449,525 A | 9/1995 | Lundberg et al. | |
| 5,509,899 A | 4/1996 | Fan et al. | |
| 5,900,457 A | 5/1999 | Duan et al. | |
| 5,925,336 A | 7/1999 | Garber et al. | |
| 6,001,910 A | 12/1999 | Blumenthal et al. | |
| 6,114,439 A | 9/2000 | Hwu et al. | |
| 6,210,853 B1 | 4/2001 | Patel et al. | |
| 6,306,419 B1 | 10/2001 | Vachon et al. | |
| 7,015,262 B2 * | 3/2006 | Leong ............... | 523/205 |

FOREIGN PATENT DOCUMENTS

| | | |
|---|---|---|
| DE | 19818958 | 11/1999 |
| EP | 0930331 | 7/1999 |
| WO | WO 97/41164 | 11/1997 |
| WO | WO 01/38448 A1 | 5/2001 |

OTHER PUBLICATIONS

"Hyrdophilic Polymer Coatings for Medical Devices—Structure/Properties, Development, Manufacture and Applications", Richard J. LaPorte, Technomic Publishing Co. Inc., pp. 57-80 & 157-165, 1997.

* cited by examiner

*Primary Examiner*—Tae H Yoon
(74) *Attorney, Agent, or Firm*—Wayne Jaeschke, Jr.

(57) ABSTRACT

Compositions, methods, devices and kits utilizing water-based hydrophilic coating formulations on medical implements. The composition for applying a coating comprises a sulfonated polyester, water, and a surface active agent. Methods for coating a medical implement comprise providing an aqueous dispersion comprising sulfonated polyester and surface active agent, contacting the medical implement with the aqueous dispersion, and drying the medical implement. Methods for acquiring a sample of bodily fluid from a patient comprise coating a needle with a sulfonated polyester, penetrating the needle into the patient, and drawing bodily fluid through the needle.

18 Claims, No Drawings

HYDROPHILIC COATINGS FOR MEDICAL IMPLEMENTS

REFERENCE TO RELATED APPLICATION

This is divisional of U.S. patent application Ser. No. 10/137,017, filed on May. 1, 2002, entitled "HYDROPHILIC COATINGS FOR MEDICAL IMPLEMENTS," by Koonwah Leong, which is fully incorporated herein by reference.

FIELD OF THE INVENTION

The present invention relates to hydrophilic coatings and the methods for applying these coatings to medical implements, such as lancing needles and the like.

BACKGROUND OF THE INVENTION

Many medical assays are in use that require use of blood or other bodily fluid samples obtained from patients by a penetrating medical implement such as a needle or cannula. In particular, diabetes patients and patients on anticoaguation therapies must frequently obtain blood samples for use in medical assays. The blood sampling devices typically involve a needle that has a small channel along which body fluid can travel once the skin is punctured by the needle. The bodily fluid sample thus obtained is applied to a test strip, introduced to a reader or sensor device, or otherwise used in an assay to monitor glucose levels, levels of therapeutic compounds present in the fluid, or other properties of the fluid.

In order to facilitate quick movement of the fluid along the channel without using a vacuum or pressure source or other external means, the surface of the needle needs to possess low contact angle property with respect to the bodily fluid. The materials from which needles can be inexpensively fabricated are tough plastics and metals. Unfortunately, the surface properties of these materials tend to be hydrophobic and do not promote capillary flow of bodily fluid through the needle.

Hydrophilic polymers, such as poly(2-hydroxyethyl methacrylate) were originally developed for use in soft, hydrophilic contact lenses and for use in the controlled release of drugs in drug delivery systems. Acrylic hydrogel polymers of this sort have been more recently been used to improve lubricity of needles during insertion into the human body. In many instances, however, a primer coating or other surface pretreatment has to be completed on a needle prior to coating the needle with a hydrophilic material such as an acrylic hydrogel. Surface pretreatment typically involves either corona discharge or plasma etching, which requires expensive equipment. This has made the use of hydrophilic coatings on needles unattractive. In other cases, crosslinking groups are introduced to the polymer coating to affect the permeability and mechanical properties of the coating. However, crosslinking of the coating frequently requires use of more complex formulation and/or use of expensive energy sources, such as a high intensity UV lamp or electron beam generator, to provide cross-linking in a previously formed coating.

U.S. Pat. No. 4,987,182 describes a method for applying a hydrophilic coating which uses a toxic and flammable solvent mixture containing isopropanol, methyl ethyl ketone and diacetone alcohol to deposit a hydrophilic coating consisting of poly(vinylbutyral) and poly(vinylpyrrolidone). Evaporation of toxic organic solvent into the atmosphere can raise environmental as well as health and safety concerns.

Polyurethane aqueous dispersions are also known as hydrophilic coating materials. However, the polymer must be highly purified in order to rid itself of any sensitizing monomeric isocyanates that may be present in the polymer. It is desirable that coatings for medical implements which come in contact with the skin to be non-allergenic and cause minimal irritation or sensitization to the skin, and urethane-based coatings have been generally unable to provide this feature.

U.S. Pat. No. 5,509,899 describes the use of poly(alkylene glycol) as a second, anti-blocking coating on top of a first hydrophilic coating. The secondary coating prevents adherence of adjacent coated devices such as catheters from adhering to each other upon contact. Unfortunately, the application of secondary, tertiary and higher numbers of coatings complicates and increases the expense of the overall coating process for medical implements, making this approach unfeasible for inexpensive needles.

Thus there is a need for a hydrophilic coating for medical devices that is non-toxic, that is easily applied in a single coating, that is very wettable and compatible to biological fluids, and is simple and inexpensive to implement. The present invention satisfies these needs, as well as others, and overcomes the deficiencies found in the background art.

Relevant Literature:

U.S. Pat. No. 5,509,899; U.S. Pat. No. 4,987,182; U.S. Pat. No. 3,734,874; U.S. Pat. No. 5,925,336; U.S. Pat. No. 6,001,910.

SUMMARY OF THE INVENTION

The present invention pertains to a water base hydrophilic coating formulations and methods of applying the coating on to a medical implement and use thereof. The subject methods and compositions provide coated medical implements or instruments prepared using a straightforward dip and dry process that requires no other surface treatments or additional coatings. The resulting dry coating is non-toxic, non-hemolytic and very wettable for facilitating extraction of body fluid from a puncture site.

The subject compositions for coating of medical implements comprise, in general terms, a sulfonated polyester, water, and a surface active agent. The sulfonated polyester comprise any sulfonated polyester or combinations of any sulfonated polyesters. In certain embodiments the sulfonated polyester may comprise a sulfonated polyalkylene phthalate, or mixtures or admixtures of sulfonated polyalkylene phthalates. More specifically, the sulfonated polyester may comprise a sulfonated polyethylene isophthalate, and in specific embodiments may comprise polyethylene-4-sodiosulfenyl isophthalate.

The surface active agent may comprise any non-ionic, anionic or cationic surface active agent or mixtures or admixtures thereof. The surface active agents may be polymeric or non-polymeric in nature. In certain embodiments the surface active agent may comprise a poly oxyethylene-co-oxypropylene block copolymer, an ethylene oxide-propylene oxide-ethylene oxide triblock copolymer, an N-oleyl-N-methyl taurate, a di-isooctylsulphosuccinate. The surface active agent may provide a contact angle of water for coating that ranges from approximately 3 to approximately 15 degrees, from approximately 7 to approximately 9 degrees, or other angle.

In certain embodiments, the composition for coating medical implements may comprise between approximately 0.5% and approximately 30% of sulfonated polyester by weight, between approximately 0.1% and approximately 5% of surface active agent by weight, and between approximately 65% and approximately 99.4% of water by weight.

The invention also provides methods for forming a hydrophilic coating on a medical implement, comprising providing an aqueous dispersion comprising sulfonated polyester and surface active agent, contacting the medical implement in the aqueous dispersion, and drying the medical implement. The invention additionally provides methods for acquiring a sample of bodily fluid from a patient, comprising coating a needle with a sulfonated polyester, penetrating the needle into the patient, and drawing bodily fluid through the needle.

Also provided by the invention are medical implements having a coating of sulfonated polyester thereon, and kit for drawing a sample of a bodily fluid, comprising the coated medical implement together with a test strip configured to receive the sample of bodily fluid. The coating on the medical implement may comprise between approximately 80% and approximately 98% weight of said sulfonated polyester, and between approximately 20% and approximately 2% by weight of surface active agent.

One object of the invention is to provide a method of acquiring a sample of bodily fluid from a patient comprising coating a needle with a sulfonated polyester and a surface active agent, penetrating the needle into the patient, and drawing the bodily fluid through the needle into a reservoir. The hydrophilic coating allowing the bodily fluid flow easily through the needle without external means.

Another object of the invention is to provide a coating with good adhesion on both plastics and metal medical implements.

Another object of the invention is to provide a coating which is relatively tough and not damaged during normal handling of medical implements.

Another object of the invention is to provide a coating which is non-hemolysing.

Another object of the invention is to provide a method of coating medical implements utilizing readily available, inexpensive materials.

Another object of the invention is to provide a coating which is non-absorbing and non-swellable in the presence of bodily fluids.

Another object of the invention is to provide a coating which is sterilizable using steam, gamma irradiation or ethylene oxide.

Another object of the invention is to provide a coating which is non-toxic and does not cause irritation or sensitization to the human skin.

Another object of the invention is to provide a coating wherein the hydrophilic properties of the coating are long lasting, allowing coated medical implements to be stored for long periods of time.

Another object of the invention is to provide a method of coating medical implements which is simple and inexpensive and environmentally friendly process, e.g. dip and dry of a water base coating.

These and other objects, advantages, and features of the invention will become apparent to those persons skilled in the art upon reading the details of the hydrophilic coating and methods of use are more fully described below.

DETAILED DESCRIPTION OF THE INVENTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It should be noted that as used herein and in the appended claims, the singular forms "a", "and", and "the" include plural referents unless the context clearly dictates otherwise. Thus, for example, reference to "a monomer" includes a plurality of such monomers and reference to "the sulfonated polyester" includes reference to one or more sulfonated polyesters and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Hydrophilic Coating Compositions.

In general, the coating formulations and compositions of the invention comprise at least one sulfonated polyester and at least one surface-active agent, in a water dispersion or solution. The concentrations and ratios of the sulfonated polyester and the surface active agent may vary depending on the polyester and surfactant chosen for the formulation of the hydrophilic coating, the particular uses of the medical implements that are coated, and other factors. The formulations and compositions of the hydrophilic coating may also vary in ratio and/or concentration due to the type of surface to be coated.

The characteristics of the hydrophilic coatings of the invention include but are not limited to, a coating that has excellent adhesion on metals, glass and plastics, which can withstand sterilization procedures, and which has a contact angle of water of less than about 20 degrees. Several formulations and compositions in accordance with the invention provide these properties, as described more fully below.

The contact angle of water measurement indicates the wettability of the surface of the hydrophilic coating. Contact angle of water measurements for a coated microneedles using the compositions and formulations of the invention range from about 1 to about 20 degrees, preferably from about 3 to about 15 degrees, and more preferably from about 7 to about 9 degrees. Lancing and microneedle medical devices coated with a hydrophilic film or coating of the present invention facilitate the acquisition of body fluids such as blood out of a puncture site.

The hydrophilic coating formulations and compositions of the invention have been found to adhere very strongly to stainless steel and plastics surfaces used in disposable needles. This adherence is mostly likely due to the nonpolar and polar groups on the sulfonated polyesters. The strong adhesion properties of the coating formulations of the invention allow for the storage of coated medical implements for many years as well as storage under adverse conditions such as high temperatures and high humidity. The coatings can also withstand conditions such as those used in steam sterilization and also the effect of gamma irradiation due to the aromatic structure of the sulfonated polyester.

One important characteristic of the hydrophilic coatings of the invention, and in particular where the coatings are used in association with lancing implements, is that the coatings do not cause hemolysis of red blood cells which can interfere with the readings or analysis of some analytes found in blood. The absence of hemolysis of red blood cells also is indicative of a coating that is biocompatible.

The concentration of the sulfonated polyester in the coating mixtures or formulations of the invention can be in the range of about 0.1% to about 40% by weight, preferably from about 0.5% to about 30%, and more preferably from about 5% by weight to about 10% by weight. The concentration is dependent on the selected sulfonated polyester, the nature medical implement to be coated, the desired coating thickness and/or other considerations. Numerous sulfonated polyester materials usable with the invention are commercially available and are discussed more fully below. Exemplary commercially available sulfonated polyester useful in the invention include Eastman AQ55S® and/or AQ55D®. A desirable physical property of a sulfonated polyester of the invention is a dispersion property with a consistency similar to that of water, i.e., of low viscosity. Another desirable property is a glass transition temperature of between about 40° C. and about 70° C., preferably between about 50° C. and about 60° C. and more preferably about 55° C.

The surface active agent in the compositions and formulations of the invention may be chosen from a variety of commercially available nonionic and anionic surfactants, such as e.g. Aerosol OT (anionic), Geropon T77 (anionic), Pluronic P105 (nonionic), and Pluronic F68 (nonionic) and the like. In some embodiments, the surface active agent may comprise a plurality of anionic and/or nonionic surfactants or any combination thereof which increases the surface wettability of the hydrophilic coating to facilitate the flow of biological fluids.

The concentration of the surface-active agent in the dry coating is in the range of about 2% to about 20% and maybe about 1% to about 15% of the total dry weight of the coating. In other words, in preparing the coating formulations, the surface active agent will comprise between about 0.1% to about 5% of the weight of the aqueous dispersion used in the formulation. Preferably, the concentration of the surface-active agent is in the range of 1% to about 3% weight based on the total weight of the aqueous dispersion.

Sulfonated Polyesters—

The sulfonated polyester may comprise any water-soluble or water-dispersible polyester material or materials having thereon sulfonate groups or salts thereof. The term "sulfonated polyester" is meant to include mixtures of various types of sulfonated polyesters, as well as individual types of sulfonated polyester. The sulfonated polyesters may be formed by condensation polymerization. The sulfonated polyesters may be homopolymers or copolymeric in nature.

The term "sulfonate group" as used herein is meant to encompass sulfonates as well as their corresponding salts with various metals. Sulfonate groups have generally the formula $-SO_3M$, wherein M is hydrogen or any metal atom or ion. Sulfonate salts in many embodiments will be based on alkali metals such as Li, Na, K, Cs, and alkaline earth metals such as Mg, Ca, Sr, Ba. However, in various embodiments, sulfonate salts based on transition metals and rare earth metals may also be used. In general, for biomedical application, sulfonate salts containing metals such as Li, Na, K, Mg, Ca, Ba, Fe, Cu, Zn, and Ag are preferred.

The sulfonate groups may be present in a polyester in the form of aryl or hetero-aryl sulfonate species or moieties. Exemplary aryl sulfonate species or moieties that may be present in the sulfonated polyester include, by way of example, phenyl sulfonates, naphthyl sulfonates, biphenyl sulfonates, diphenyl ether sulfonates, diphenyl thioether sulfonates, diphenyl alkylene sulfonates, bisphenol sulfonate, and other aryl sulfonates.

In many embodiments the sulfonated polyesters comprise condensation polymer products of diester monomers and glycol monomers, one or both of which may include one or more sulfonate group thereon. Aryl sulfonate groups that may be present in diester and/or glycol monomers include aryl sulfonate species or moieties that may be present in the sulfonated polyester include phenyl sulfonates, naphthyl sulfonates, biphenyl sulfonates, diphenyl ether sulfonates, diphenyl thioether sulfonates, diphenyl alkylene sulfonates, and like aryl sulfonate species as noted above. Monomers containing unsulfonated aryl groups may also be present in copolymer compositions.

Sulfonated polyesters made from condensation polymerizations may, in certain embodiments comprise the formula (1) wherein X comprises any aryl sulfonate, Y comprises any alkylene or arylene glycol, and n is an integer having a value between 3 and 100,000, and more preferably between about 10 and about 10,000.

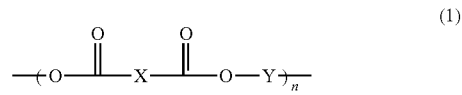

(1)

The sulfonated polyester (1) may be prepared, for example, from a condensation reaction of one or more types of aryl sulfonate diester, diacid or diacid chloride monomer, and one or more types of alkylene or arylene glycol monomer. More than one type of diester comonomer and/or glycol comonomer may be used in the preparation of the sulfonated polyester. In other embodiments, the group X in structure (1) may comprise any alkylene or arylene group, while Y comprises an aryl sulfonate group. In still other embodiments, X and Y may each comprise an aryl sulfonate group. The polymers may be formed via condensation from aryl sulfonate monomers that each include an ester, acid or acid chloride functionality, and a hydroxyl functionality.

An exemplary sulfonated polyester usable with the invention is shown by the structure (2)

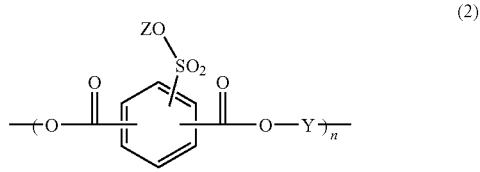

(2)

wherein Y is any alkylene or arylene group, Z is a hydrogen, metal atom, alkyl, alkoxy, aryl, aryloxy, or other group, and n is an integer having a value between 3 and 100,000, and more preferably between about 10 and about 10,000. In certain embodiments, Z may comprise another aryl sulfonate group such as a phenyl sulfonate, naphthyl sulfonate, biphenyl sulfonate, diphenyl ether sulfonate, diphenyl thioether sulfonate, diphenyl alkylene sulfonate, bisphenol sulfonate, or other aryl sulfonate.

The aryl sulfonate diester may comprise, for example, a sulfonated orthophthalate, isophthalate or terephthalate ester monomer, or various derivates or salts thereof. The alkylene or arylene glycol monomer may comprise, for example, ethylene glycol, propylene glycol, butylene glycol, a bisphenol compound, or any of a variety of derivatives or salts thereof. These types of monomers may be used in various combinations to provide various types of sulfonated polyesters. Exemplary aryl sulfonate monomers include, by way of example, sufonylphenyl-dicarbomethoxybenzenesulfonates, sulfophenoxy-dicarbomethoxybenzenesulfonates, and sulfonylnaphthyl-dicarbomethoxybenzenesulfonates. The preparation of sulfonated polyesters with these monomers is described in U.S. Pat. No. 3,734,874, the disclosure of which is incorporated herein by reference.

In specific embodiments of the invention, the sulfonated polyester may comprise a polymer made from a sulfonated phenyl sulfonate ester of a phthalate compound and an alkylene glycol, such as the sulfonated polyester (3)

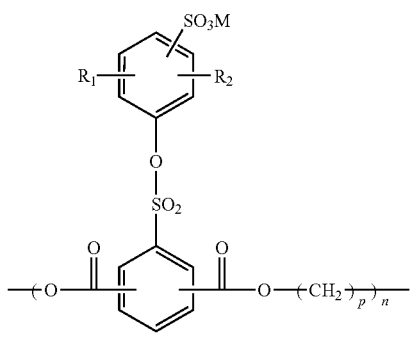

(3)

wherein M is a hydrogen, metal atom, alkyl, aryl, or aryl sulfonate group, and $R_1$ and $R_2$ each individually comprise hydrogen, alkyl, aryl, alkoxy, aryloxy, sulfonate or aryl sulfonate, p is an integer having a value between 1 and 10, and n is an integer having a value between 3 and 100,000, and more preferably between about 10 and about 10,000.

In one embodiment of the invention, the sulfonated polyester is a polyethylene sodiosulfonylphenyl isophthalyl sulfonate having the general formula (4)

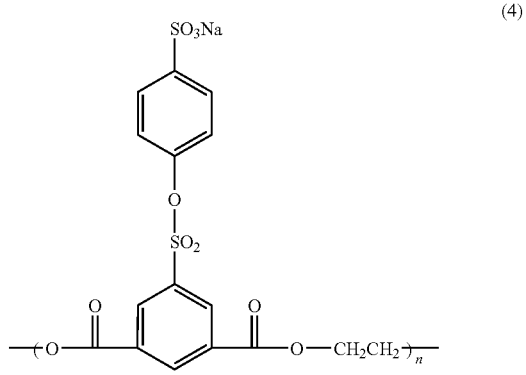

(4)

The sulfonated polyester (4) may be prepared by a polymeric condensation reaction of ethylene glycol with 4-sodiosufonylphenyl-3,5-dicarbomethoxybenzenesulfonate. A portion of the 4-sodiosufonylphenyl-3,5-dicarbomethoxybenzenesulfonate. monomer may be replaced in part with un-sulfonated phthalate monomers such as 3,5-dicarbomethoxybenzene and/or 1,4-dicarbomethoxybenzene, to reduce the number or level of sulfonate groups present in the sulfonated polyester. The 4-sodiosufonylphenyl-3,5-dicarbomethoxybenzenesulfonate monomer may be replaced, in whole or in part, by various other aryl sulfonate diesters as noted above. The preparation of sulfonated polyesters of this sort is well known and is described in U.S. Pat. No. 3,734,874 noted above, and elsewhere. Sulfonated polyesters made from aryl sulfonate monomers are commercially available from various sources.

Surface Active Agents—

The surface-active agents useful for the present invention are surfactants which lower the contact angle of water to below about 20 degrees after being incorporated into the sulfonated polyester. Preferably, the surface-active agent is a solid or waxy solid, which minimizes its migration or removal from the surface of the coating. The solubility of the surface-active agent in water is preferably to be such that it is difficult to dissolve or disperse in water. Also preferable surface active agents are those which are considered environmentally friendly and biodegradable.

Examples of some suitable surface active agents usable with the invention include: (a) natural surfactants such as e.g., casein, gelatin, tragacanth, waxes, enteric resins, paraffin, acacia, gelatin, cholesterol esters and triglycerides; (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids; and (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, calcium carboxymethylcellulose, and sodium dodecylsulfate. In certain embodiments cationic surfactants may alternatively or additionally be utilized.

Various blends of natural, nonionic and/or anionic surface active agents may be utilized in the formulation of the hydrophilic coating of the invention. Additional examples of anionic surfactant groups include sulfonic acid salts, alcohol sulfates, alkylbenzene sulfonates, phosphoric acid esters, and carboxylic acid salts. These anionic surfactants tend to be good solubilizers and have good wetting property.

Preferred anionic surface active agents for use with the invention include GEROPON™ T77 (N-oleyl-N-methyl taurate, sodium salt, available from Rhodia, Inc.) and Aerosol OT™ (di-isooctylsulphosuccinate, sodium salt, available from Cytec Industries, Inc.). Both of these anionic surface active agents have strong wetting and dispersing properties.

Nonionic surfactants are characterized by hydrophilic head groups that do not ionize appreciably in water. Examples of preferred nonionic surfactants include polyoxyethylenated alkylphenols, alcohol ethoxylates, alkylphenol ethoxylates, and alkanolamides. Nonionic surfactants also tend to be good solubilizers and are relatively nontoxic.

More specifically, examples of suitable nonionic surface active agents include one or of the following surfactants: polaxomers, such as Pluronic™ F68, F108 and F127, which are block copolymers of ethylene oxide and propylene oxide available from BASF; poloxamines, such as Tetronic™ 908 (T908), which is a tetrafunctional block copolymer derived from sequential addition of ethylene oxide and propylene oxide to ethylene-diamine available from BASF; Triton X-100, which is an alkyl aryl polyether, available from Union Carbide/Dow Chemical Co. Poly (oxyethylene-co-oxypropylene) block polymer, Pluornic™ F68 and Pluornic™ P105 (ethylene oxide-propylene oxide-ethylene oxide) triblock copolymer are an excellent solubilizers and are generally considered non-hemolytic.

The surface active agent maybe chosen from a range of commercially available surfactants like those disclosed above and in particular, e.g. Aerosol™ OT, Geropon™ T77, Pluronic™ P105, and Pluronic™ F68. Various combinations of these anionic and nonionic surfactants give satisfactory results in the formulation of the coating of the invention.

Hydrophilic Coating Methods—

The method of coating medical implements with a hydrophilic coating in accordance with invention comprises coating the medical implement with an aqueous solution comprising a dispersion or solution of a sulfonated polyester and a surface active agent. The method of coating medical implements may further comprise drying the coated medical implement until the coating has achieved a desired level of hardness and strongly adheres to the medical implement. Coating the medical implement may comprise spraying, dipping, and/or rolling the aqueous dispersion or solution of the hydrophilic coating onto the medical implement. Other coating techniques known to those skilled in the art of coating steel and plastic medical devices are also useful in the methods of the invention.

The drying time will depend on the drying temperature, with higher drying temperatures requiring shorter drying times, and vice versa. Other factors which play a role in determining appropriate drying times, are the thickness of the coating desired, the efficiency of removing excess solution from the medical implement, and the size and shape of the device to be coated. Persons skilled in the art can determine a suitable combination of drying temperatures and drying time for a specific coating in accordance with the invention.

In general, the drying time for medical implements, such as a capillary or microneedle, dip coated with the hydrophilic compositions described herein, range from about 5 minutes to one hour and preferably from 10 minutes to about 30 minutes, when air-dried at 45° C. to about 65° C. Faster drying cycles can be achieved at temperatures of about 65° C. to about 70° C.-80° C. with sufficient drying of the coating in about 5 minutes to about 15 minutes. During this dip and dry method of coating a medical implement, no toxic solvents or fumes are released, which is an improvement over other coating currently available.

In one embodiment, the method of coating a microneedle comprises dipping a the microneedle into an aqueous dispersion comprised of approximately 5% to about 10% of a sulfonated polyester, such as EASTMAN™ AQ55S or AQ55D by weight, and approximately 0.1% to about 3% of at least one surface active agent, such as Aerosol™ OT (di-isooctyl-sulphosuccinate), Geropon™ T77 (N-oleyl-N-methyl taurate), Pluronic™ P105 (ethylene oxide-propylene oxide-ethylene oxide triblock copolymer), and Pluronic™ F68 (poly oxyethylene-co-oxypropylene block polymer) and the like. The excess aqueous solution is removed from the microneedle and the coated microneedle is allowed to dry for 20 minutes at 50-60° C.

Kits

The invention also provides kits for coating medical implements with a sulfonated polyester, and kits containing medical implements such as microneedles that have a sulfonated polyester coating thereon. The kits may comprise, for example, a vial or other container of an aqueous dispersion or solution of sulfonated polyester and a suitable surfactant having a composition as described above, together with one or more needles or other medical implements that may be coated by dipping into the solution followed by drying in the manner described above. The kit may further comprise printed instructions for coating the medical implements with the sulfonated polyester dispersion, and drying the coated implements.

In other embodiments, the kit may comprise one or more medical implements such as needles having a coating of sulfonated polyester thereon. The kit may further comprise printed instructions for use of the needles for obtaining a sample of blood or other bodily fluid. The kits may still further comprise one or more tests strips, or a monitor or sensor, configured to receive a bodily fluid sample.

EXAMPLES

The sulfonated polyester utilized in the following examples has a glass transition temperature of approximately about 55° C., and is based on the sulfonated polyester (4) discussed above. This sulfonated polyester is commercially available from Eastman Chemical Co. under the product name of either Eastman AQ55S or AQ55D. AQ55S is the solid form and the AQ55D is a 28% water dispersion of AQ55S. The concentration of the polyester in the aqueous formulation of the coating mixture can be in the range of 0.5-30%, and preferably from about 5 to 10% by weight in water. This sulfonated polyester is described in U.S. Pat. No. 3,734,874 noted above.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Centigrade, and pressure is at or near atmospheric.

Example 1

Wettability and Tackiness of various Hydrophilic Formulations.

For this Example, formulations were prepared and tested on both a stainless steel surface and on a plastic PET film. The formulations were tested for tackiness, durability and wettability. TABLE 1 shows the parts/volume of aqueous stock sulfonated polyester solution to parts of surfactant stock solution to parts of water. The sulfonated polyester stock solution was prepared with 28% by weight of solid in water (EASTMAN AQ 55D is 28% solid sulfonated polyester by weight in water. All of the surfactant stock solutions were prepared as a 3% by weight of surfactant in water. Surfactants tested were Aerosol OT (anionic), Geropon T77 (anionic), Pluronic P 105 (nonionic), Pluronic F68, Silwet L7600 and glycerol as a control. The chemical composition of these surfactants is discussed above.

The hydrophilic coating formulations were prepared by thoroughly mixing the appropriate amount (parts) of sulfonated polyester and surfactant stock solutions with the specified amount of water as listing in TABLE 1. The surface to be coated was dipped into the aqueous dispersion of the hydrophilic coating, followed by the removal of excess coating from the surface. The surface was then allowed to dry for 5 minutes at 80-90° C. in a forced air oven.

The tackiness of the coating was determined by physical touching of the surface coating and the wettability of the surface coating was determined by measuring the contact angle of water with a Goniometer from Rame Hart Inc. To test the durability of the coatings, the coatings were washed three times with water followed by again measuring the wettability of the coating.

TABLE 1 shows that the control samples, samples 1 and 9 did not form a suitable hydrophilic coating on either stainless steel or plastic. All of the samples, except for samples 3, 4 and 7, were found to be non-tacky after drying.

Tests were also completed on formulations which comprised more than one surfactant. Formulations with a combination of Aerosol OT and Pluronic P 105 or of Geropon T77 and Pluronic P105 were also found to be non-tacky and wettable as shown with samples 13-16 of TABLE 1.

This example demonstrates that coatings with surfactants in the final concentration range of about 1% to about 3% by weight of surfactant in the aqueous formulation (which is equivalent to about 2% to about 20% of the total solid weight of the dried formulation) gave desirable results for being durable, non-tacky and very wettable.

TABLE 1

Tackiness and Wettability of Selected Hydrophilic Coatings

| Sample Number | Formulation of Hydrophilic Coating Sulfonated Polyester:Surfactant:water (Parts per Volume of Stock Solutions) | | Tack | H₂0 wettable | H₂0 wettable after washes |
|---|---|---|---|---|---|
| 1 | 1:0:2 | Control | NO | NO | — |
| 2 | 1:1:1 | Surfactant = Aerosol ™ OT | NO | YES | YES |
| 3 | 1:2:0 | Surfactant = Aerosol ™ OT | YES | YES | YES |
| 4 | 1:2:3 | Surfactant = Aerosol ™ OT | YES | YES | Less |
| 5 | 1:1:1 | Surfactant = Geropon ™ T77 | NO | YES | YES |
| 6 | 2:1:3 | Surfactant = Geropon ™ T77 | NO | YES | Less |
| 7 | 1:1:1 | Surfactant = Silwet ™ L7600 | YES | YES | YES |
| 8 | 1:1:1 | Surfactant = Pluronic ™ P105 | Slightly | YES | YES |
| 9 | 1:1:1 | Surfactant = Pluronic ™ F68 | NO | YES | Less |
| 10 | 1:2:0 | Surfactant = Pluronic ™ F68 | NO | YES | Less |
| 11 | 1:1.5:0.5 | Surfactant = Pluronic ™ F68 | NO | YES | YES |
| 12 | 1:1:1 | Surfactant = Glycerol | NO | NO | — |
| 13 | 2:1(AEROSOL ™ OT):1 (PLURONIC ™ P105):2 | | NO | YES | YES |
| 14 | 2:0.5 (AEROSOL ™ OT):0.5 (PLURONIC ™ P105):3 | | NO | YES | YES |
| 15 | 2:1(GEROPON ™ T77):1 (PLURONIC ™ P105):2 | | NO | YES | YES |
| 16 | 2:0.5 (GEROPON ™ T77):0.5 (PLURONIC ™ P105):3 | | NO | YES | YES |

Example 2

Contact Angle of Water of the Hydrophilic Coatings

This example demonstrates the wettability of various formulations of the hydrophilic coating on a plastic surface, 5 mil Melinex polyester film available from DuPont. The method of coating the Melinex film was similar to the method described in Example 1. The stock solutions of the sulfonated polyester (AQ55D) and the surfactants used in this example were prepared as described in example 1.

TABLE 2 shows the contact angle of water measurements of various hydrophilic coatings of the invention as well as Melinex coated with an antifog coating (3M™ Antifog, Part# 3MM 9962/387) as a control. The % of sulfonated polyester by weight of total dry weight of the composition was 90-95% for all the formulations presented in TABLE 2. The percentages of surfactant given in TABLE 2 are the percent of surfactant by weight of the total dry weight of the hydrophilic coating.

Two to five contact angle of water tests, which included both left and right side of the water droplet contact angle measurements, were completed for the hydrophilic coatings represented in TABLE 2. TABLE 2 gives the ranges of contact angle of water measurement values as well as the average measurement for hydrophilic coatings A1-E2.

TABLE 2

Contact Angle of Water Measurements

| Sample | Description | Range of 4 Values | Average Value |
|---|---|---|---|
| Control | 3M Anti-fog | 17.6–23.9 | 21 |
| A1 | 10% AEROSOL ™ OT | 3.9–13.5 | 7 |
| A2 | 5% AEROSOL ™ OT | 5.2–11.9 | 9 |
| B1 | 10% PLURONIC ™ P105 | 6–9.5 | 8 |
| B2 | 5% PLURONIC ™ P105 | 7–12 | 9 |
| C1 | 10% GEROPON ™ T77 | 5.9–8.8 | 7 |
| C2 | 5% GEROPON ™ T77 | 7.5–8.8 | 8 |
| D1 | 5% AEROSOL ™ + 5% PLURONIC ™ P105 | 7–8 | 8 |
| D2 | 2.5% AEROSOL ™ + 2.5% PLURONIC ™ P105 | 6.6–8.5 | 7 |
| E1 | 5.0% AEROSOL ™ + 5.0% GEROPON ™ T77 | 5–10 | 8 |
| E2 | 2.5% AEROSOL ™ + 2.5% GEROPON ™ T77 | 6–8 | 7 |

This example provides further evidence of the wettability of the hydrophilic coatings of the invention as well as the a method of applying the coating to a plastic surface.

Example 3

Hemolysis Test

The hydrophilic coating with the formulation of 2 part AQ55D (28%); 0.5 part Aerosol OT (3%); 0.5 part Pluronic P105 (3%); 3 part water was tested for hemolytic activity against human whole blood.

In order to maximize the surface contact between the hydrophilic coating and blood volume, capillary tubes were used to conduct this experiment. Plastic capillary tubes having 1 mm ID were filled with the hydrophilic coating and allowed to stand for 5 seconds. Excess coating solution was drained out by touching the end of the capillary tube with an absorbent tissue paper. The capillary tubes were allowed to dry for at least 20 hours at room temperature inside a tightly sealed container containing copious amount of desiccants.

A sample of normal whole blood from a human donor was used. The dry capillary tubes coated on the inside with the hydrophilic coating mixture were filled with the whole blood sample by dipping the tubes in the blood at a tilted angle. The end of each tube was quickly sealed with a tube sealing compound available from Chase Instrument Corp. The blood filled tubes were laid on their sides and allowed to incubate at room temperature for 0, 1, 2, 3, 4, and 5 minutes without disturbance. At the end of each incubation period, a blood filled capillary tube was put on a Readacrit Centrifuge available from Becton Dickenson and the blood cells were spun down for about 1-2 minutes.

After centrifugation, the plasma was observed for any yellow of red tint which would indicate hemolysis. No color variations were seen in the plasma of any of the samples, including the 5 minute incubation time point.

Thus this experiments demonstrated that the hydrophilic coating was non-hemolytic.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for acquiring a sample of bodily fluid from a patient, comprising;
   (a) coating a needle with a composition comprising a sulfonated polyester;
   (b) penetrating said needle into said patient; and
   (c) drawing said bodily fluid through said needle.

2. The method of claim 1 wherein said sulfonated polyester comprises a sulfonated poly(alkylene phthalate).

3. The method of claim 2 wherein said sulfonated polyester comprises a polymeric compound having the structure

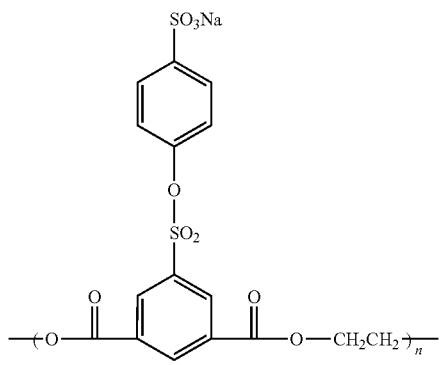

where n is an integer having a value between 3 and 100,000.

4. The method of claim 2 wherein said sulfonated polyester comprises a sulfonated poly(ethylene isophthalate).

5. The method of claim 2 wherein said sulfonated polyester comprises poly(ethylene 4-sodiosulfenyl isophthalate).

6. A method for forming a hydrophilic coating on a medical implement, comprising:
   (a) providing an aqueous disperson comprising sulfonated polyester and surface active agent;
   (b) contacting said medical instrument with said aqueous disperson; and
   (c) drying said medical implement,
   wherein said providing said aqueous dispersion comprises providing a composition comprising:
      (a) between approximately 0.5% and approximately 30% of sulfonated polyester by weight;
      (b) between approximately 0.1% and approximately 5% of surface active agent by weight; and
      (c) between approximately 65% and approximately 99.4% of water by weight.

7. The method of claim 6 wherein drying said medical implement comprises; heating the coated medical implement at about 60° C. to about 120° C.

8. The method of claim 6 wherein said medical implement comprises a lancing implement.

9. The method of claim 8 wherein said lancing comprises a microneedle.

10. The method of claim 1 further comprising coating said needle with a surface active agent in the presence of said sulfonated polyester.

11. The method of claim 1, further comprising drying said needle to provide a solid coating thereon.

12. The method of claim 11 wherein said drying comprises heating said needle to a temperature of approximately about 60° C. and 120° C.

13. The method of claim 1, wherein said coating is carried out using a composition comprising:

(a) between approximately 0.5 % and approximately 30 % of sulfonated polyester by weight;

(b) between approximately 0.1 % and approximately 5 % of surface active agent by weight; and (c) between approximately 65 % and approximately 99.4 % of water by weight.

14. The method of claim 13, wherein said coating comprises dipping said needle in said composition.

15. The method of claim 11, wherein said solid coating comprises between approximately 80 % and approximately 98 % weight of said sulfonated polyester, and between approximately 20 % and approximately 2 % by weight of surface active agent.

16. The method of claim 15 wherein said sulfonated polyester comprises a sulfonated poly(alkylene phthalate).

17. The method of claim 16 wherein said sulfonated polyester comprises a sulfonated poly(ethylene isophthalate).

18. The method of claim 17 wherein said sulfonated polyester comprises poly(ethylene 4-sodiosulfenyl isophthalate).

* * * * *